United States Patent [19]

Morris

[11] 4,010,358

[45] Mar. 1, 1977

[54] APPARATUS AND PROCESS FOR MEASURING FUEL OCTANE NUMBERS

[75] Inventor: William Emery Morris, Wilmington, Del.

[73] Assignee: E. I. Du Pont de Nemours and Company, Wilmington, Del.

[22] Filed: June 19, 1975

[21] Appl. No.: 588,645

[52] U.S. Cl. .............................. 235/151.35; 73/35; 44/2
[51] Int. Cl.² ...................................... G01N 33/22
[58] Field of Search ..... 235/151.35, 151.3, 151.34; 73/35; 44/2

[56] References Cited

UNITED STATES PATENTS

| | | | |
|---|---|---|---|
| 3,318,136 | 5/1967 | Payne et al. | 73/35 |
| 3,469,954 | 9/1969 | Hoffman | 44/2 |
| 3,511,980 | 5/1970 | May | 235/151.3 X |

*Primary Examiner*—Edward J. Wise
*Attorney, Agent, or Firm*—James A. Costello

[57] ABSTRACT

An improved process and apparatus for measuring fuel octane numbers in a knock test engine of a multiplicity of fuels, using at least one fuel of known octane number as a reference, wherein fuel feed means, memory means, and calculating means cooperate so that the fuel feed means selects the fuel source and the fuel feed-rate for that fuel source, the memory means receives the knock intensity values generated in the test engine and the corresponding fuel feed-rate settings, the calculating means (a) determines the approximate feed-rate setting that corresponds to the maximum knock intensity, (b) provides a series of feed-rate settings bracketing said approximate feed-rate setting and generates a corresponding set of knock intensity values, (c) determines the refined feed-rate setting that corresponds to maximum knock intensity, (d) sends said setting to the memory means for storage, and (e) from the knock intensities that are generated during subsequent comparison of the fuels of known and unknown octane numbers at the stored fuel feed-rate setting, the octane numbers of the unknown fuels are calculated by comparison of their knock intensities with those of the known fuel(s).

1 Claim, 4 Drawing Figures

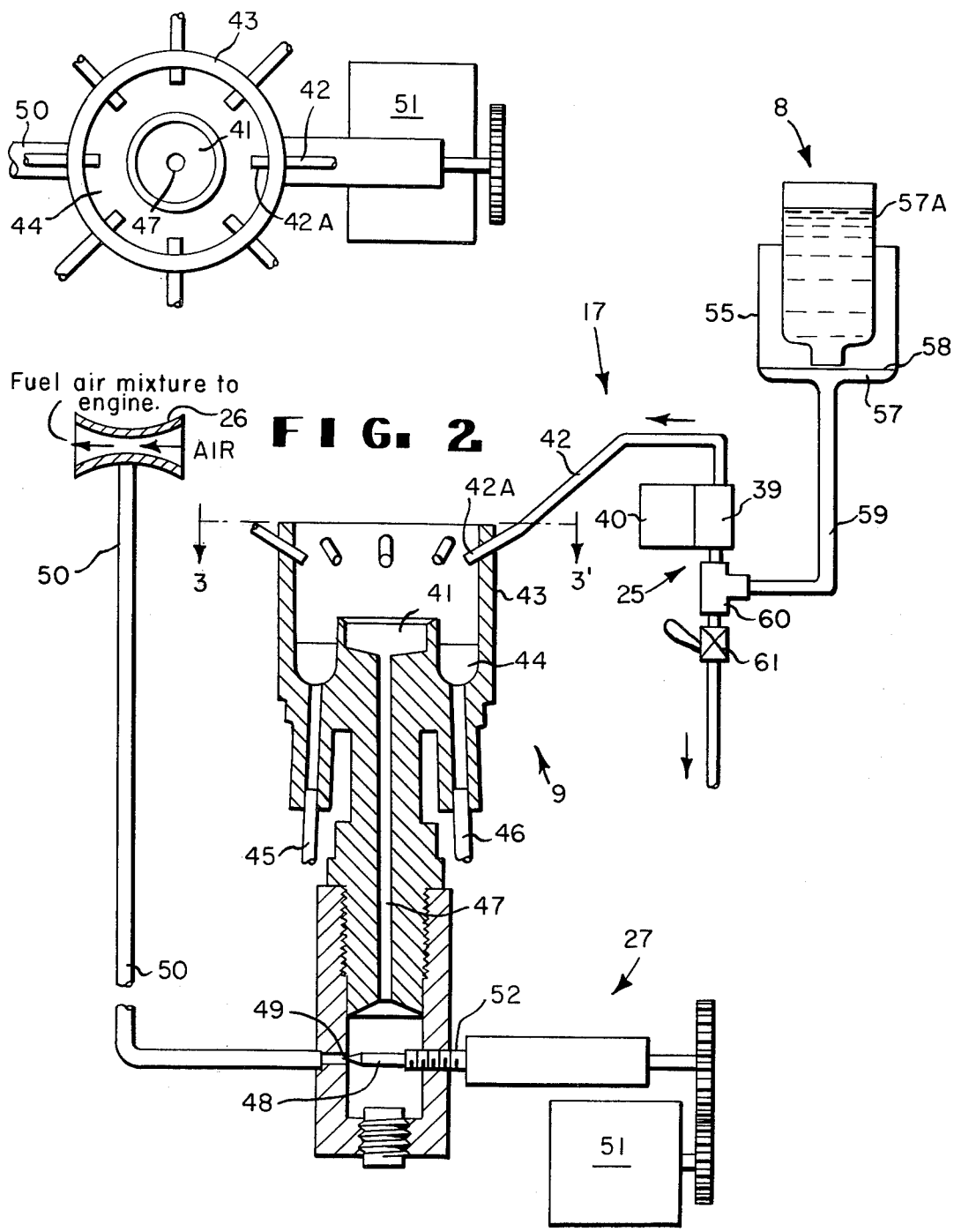

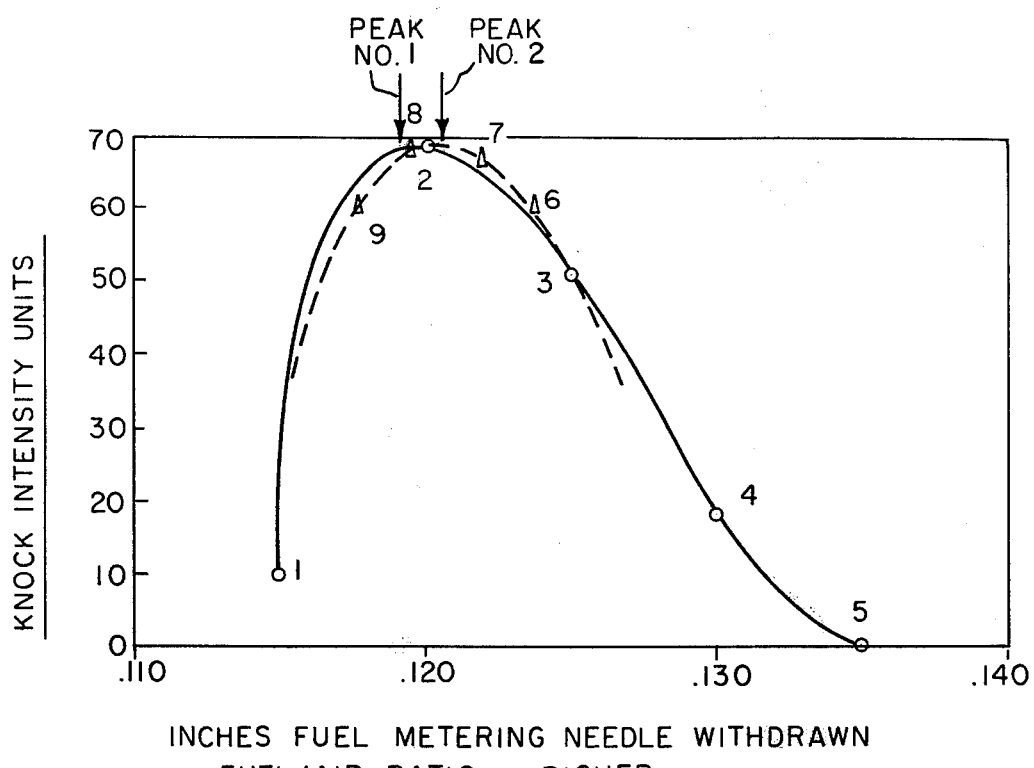

APPARATUS AND PROCESS FOR MEASURING FUEL OCTANE NUMBERS

BACKGROUND OF THE INVENTION

This invention concerns a novel method and apparatus for determining fuel octane numbers. Many methods and devices for determining fuel octane numbers are known. However, none of them is entirely satisfactory because each method or device either requires too much time or is not accurate enough. Engine drift, which is inherent in all test engines, is an important cause of these problems. Engine drift occurs when a knock test engine that is run on a particular fuel with constant running and measuring conditions generates knock intensity signals which go through intensity changes. Such intensity changes occur according to deposit build-up and flaking, changes in operating temperature, changes in voltage supplied to the knock measuring equipment and mechanical shifts in the engine. Because of the changes occurring during the normal manual octane test procedure, the operator has many opportunities to exert bias by selecting the moment at which the reading is taken.

SUMMARY OF THE INVENTION

This invention relates to an apparatus and process for measuring the octane numbers of fuels by comparing knock intensities of fuels with known octane numbers to knock intensities of fuels with unknown octane numbers in a knock test engine. The invention overcomes the weaknesses of the prior art by rapidly providing accurate octane numbers through minimization of error caused by engine drift and operator bias.

The novel process of this invention is an improvement in a process for determining fuel octane numbers from knock intensity signals generated by a test engine by comparing knock intensities of fuels of unknown octane numbers against knock intensities of fuels of known octane numbers, the improvement comprising in sequence, i. operating the test engine on each fuel at a series of feed-rate settings for a time sufficient to generate a knock intensity signal for each fuel at each of the feed-rate settings, said knock intensity signals bracketing the feed-rate setting which gives the maximum knock intensity for each fuel, ii. calculating the approximate setting for each fuel at which the maximum knock intensity signal is generated, iii. operating the engine on each fuel at a narrower series of feed-rate settings then employed in (i), such settings bracketing the approximate maximum knock intensity setting as determined in (ii), to produce a refined feed-rate setting at which the maximum knock intensity signal is generated for each fuel, iv. storing the refined feed-rate setting of maximum knock intensity, v. operating the test engine on each fuel at the stored refined feed-rate setting at which the maximum knock intensity is generated, for a time sufficient to generate a new knock intensity signal, the test engine being operated on the fuels of known and unknown octane numbers in alternating sequence, and vi. calculating the octane numbers of the fuels of unknown octane numbers by comparing the new knock intensity signals produced in (v).

In the improved apparatus for determining the octane numbers of fuels of unknown octane numbers that are fed to a knock test engine from a source of fuels of known and unknown octane numbers wherein said knock test engine generates knock intensity signals for each fuel of known and unknown octane numbers over a range of fuel feed-rates, said apparatus comprising:

fuel feed means adapted to feed a fuel of known octane number and a fuel of unknown octane number to the test engine, said means comprising a fuel selection control device, a fuel rate metering device, and a fuel/air mixing device, a knock intensity receptor that accepts knock intensity signals from the test engine and transmits them to memory means, memory means that store knock intensity signals transmitted by the receptor and transmit such signals to the calculating means, calculating means that compare knock intensity signals of known and unknown octane fuels to determine unknown octane numbers, the improvements which comprise the fuel feed means, memory means, and calculating means being adapted to cooperate in operational sequence wherein, i. the fuel feed means variably selects each fuel from said multiplicity of fuels and applies a series of predetermined fuel feed-rate settings at which each of said fuels is fed to the knock test engine, ii. the memory means receives the knock intensity values generated by the test engine and the corresponding fuel feed-rate settings for use by the calculating means, iii. the calculating means determines the fuel feed-rate setting at which the maximum knock intensity is generated for each fuel, sends that setting to the memory means which stores the approximate fuel feed-rate setting corresponding to maximum knock intensity as determined for each fuel by the calculating means, iv. the calculating means determines a series of fuel feed-rate settings in a range that brackets the approximate fuel feed-rate setting at which the maximum knock intensity is generated for each fuel as already determined in (iii), v. the calculating means directs the fuel feed means to apply the settings of (iv) to generate corresponding knock intensity signals and to determine a refined new maximum knock intensity feed-rate setting for use in the comparison testing of fuels, and vi. the calculating means determines the octane number of each unknown fuel by comparing the knock intensity signals of the known and unknown fuels in sequence, said knock intensity signals being generated at the stored new maximum knock intensity feed-rate settings of (v).

BRIEF DESCRIPTION OF THE DRAWINGS

FIG. 2 shows in more detail an embodiment of schematic FIG. 1 represented by numerical symbols 8, 25, 17, 9, 27, 50 and 26.

FIG. 3 is a view through section 3—3' of FIG. 2.

FIG. 4 is a graph depicting the development of an approximate maximum knock intensity fuel feed-rate and a refined maximum knock intensity fuel feed-rate.

DETAILS OF THE INVENTION

Figure 1:
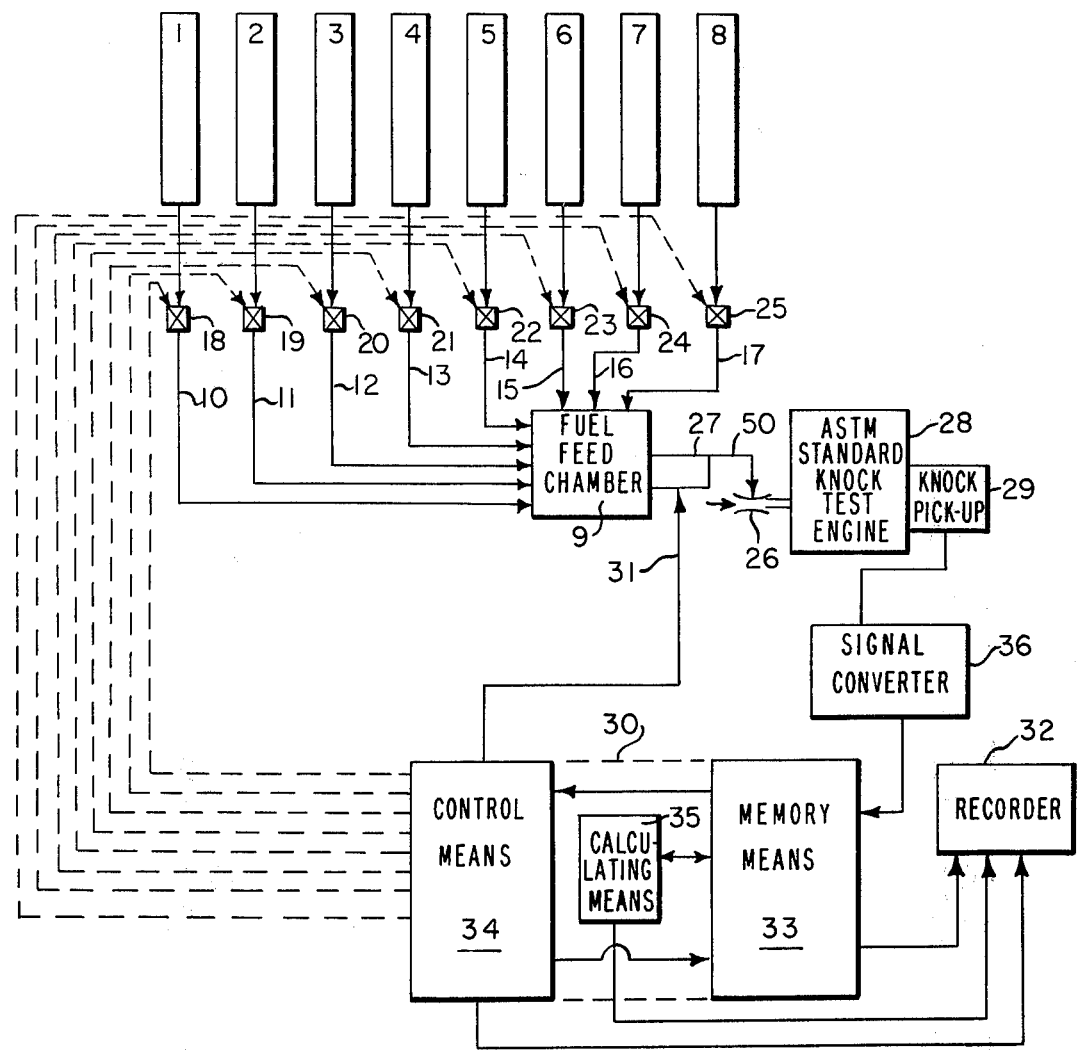
FIG. 1 is a schematic diagram of an octane number determining apparatus that is an embodiment of this invention.

The fuel source used in this invention normally includes a multiplicity of fuel reservoirs say, 2 to 15, of octane numbers unknown but expected to be in a certain range and at least one, preferably two, reference fuels of known octane number. One reference fuel can be used when it is a prototype fuel as described in ASTM D-2885 and a direct match procedure is used. Preferably, two reference fuels are used that span the limits of an expected octane number range.

Reference fuels can be primary reference fuels for finding octane numbers in the 0 to 100 range or in the 100 to 120 range. Primary reference fuels in the 0 to 100 octane number range consist of mixtures of 2,2,4-trimethylpentane (isooctane) and n-heptane having their octane numbers characterized by their volume percent content of isooctane. Primary reference fuels in the 100 to 120 octane number range consist of mixtures of isooctane and varying amounts of tetraethyllead, as is well known in the art.

In the following discussion of the Figures, the fuel feed means is described with particular attention to its individual components: a fuel selection control device 34, fuel feed chamber 9, fuel-rate metering device 27 and fuel/air mixing throat 26, together with the network by which these components communicate with each other and multiple fuel sources 1 to 8. It will be appreciated that an ASTM Standard Knock Test Engine is operated at constant piston stroke and engine speed, so it uses air at a rate depending only on atmospheric pressure. Thus, a variation of fuel feed is essentially a fuel/air ratio variation.

In the following discussion, the knock intensity receptor is described in terms of its individual components knock pick-up 29, and signal converter 36. One suitable converter averages signals taken one second apart as the basis for knock intensity values.

In the following discussion, fuel-rate metering device 27 controls the rate of flow of fuel to the air intake. Any apparatus that performs this function can be employed and will be obvious to one skilled in the art. The apparatus can operate by sucking fuel from the feed chamber to control its surface level or by raising or lowering the whole fuel feed chamber. Ordinarily, such a device operates by controlling the eclipse of a fuel-metering hole by a slide across the hole or by a cone axially movable into the hole.

In FIG. 1, fuel reservoirs 1 to 8 communicate with fuel feed chamber 9 through lines 10 to 17 having interposed fuel shut-off valves 18 to 25 selectively responsive to control means 34. Control means 34 is adapted also to send definite fuel feed-rate settings via line 31 to feed-rate metering device 27.

Additional details concerning the cooperation of items 17 (42), 9, and 27, are provided in coassigned patent application entitled "Apparatus For Measuring Fuel Octane Numbers," bearing U.S. Ser. No. 588,644, now U.S. Pat. No. 3,969,922 filed June 19, 1975.

The fuel feed means includes any switching device adapted to select a fuel from a reservoir which is responsive to a suitable selective control signal. It is known, for instance, to use a single selector switch to select a reservoir with fuel for test according to one of a variety of selector control signals. However, it is preferred that each reservoir communicates with the fuel chamber through a separate fuel feed line having its own shut-off valve interposed therein, as in FIG. 1.

Fuel is admitted by fuel-rate metering device 27 to test engine 28 via line 50 and fuel/air mixing throat 26. Knock pick-up 29 provides a signal characteristic of knock intensity in the test engine through the analog-to-digital signal converter 36 for transmission to memory means 33.

Memory means 33 is adapted to accept: reservoir selection signals also sent by means 34 to selector valves 18 to 25; feed-rate settings also sent by means 34 to fuel feed-rate metering device 27; and knock intensity signals are transmitted via signal converter 36. In memory means 33, knock intensities are correlated with the feed-rate settings and fuel reservoirs producing them. Transfer of these correlated signals is made to calculating means 35 from which are received optimum feed-rate settings, corresponding to maximum knock intensities, for storage and release to control means 34 upon demand.

Calculating means 35 is adapted to accept knock intensity signals correlated with feed-rate settings and reservoir selection from memory means 33, to calculate the maximum knock intensity from data points of knock intensity signals against fuel feed-rate settings, to correlate an approximate fuel feed-rate setting with the maximum knock intensity, to transfer that feed-rate setting to memory means 33, to provide additional maximum feed-rate settings for further data points of knock intensity against fuel feed-rate settings, to correlate a refined optimum fuel feed-rate setting with the maximum knock intensity calculated from the further data points and to transfer that setting to memory means 33.

Calculating means 35 is also adapted to accept new knock intensity signals resulting from knock intensity operation on each fuel at its maximum knock intensity fuel feed-rate setting, to compare the new knock intensity signal generated for each fuel having an unknown octane number with corresponding new signals generated for the reference fuels of known octane number, and to calculate the octane number of each fuel of unknown octane number as a function of the relation of its new knock intensity signal to the reference fuel new knock intensity signals. Calculating means 35 is also operatively linked to recorder 32 which records the calculated octane numbers corresponding to fuels from each reservoir. Recorder 32 can be a printer or teletype machine.

In FIG. 1, control means 34, calculating means 35 and memory means 33 are each linked to recorder 32. As will be appreciated by those skilled in the art, there are various types of apparatus that will perform the functions ascribed to elements 32, 33, 34 and 35. It is preferred that all of these elements be combined into an integrated unit and computer 30 is meant to typify such a combination of apparatus elements 33, 34 and 35. Each of said elements is operatively attached to a clock-operated programmer which is not shown. The programmer defines a series of different fuel feed-rate settings each of which results in engine knock at a fixed compression ratio and times the functions of these means.

The computer can be programmed for relatively short signal measuring times, such as the last 10 to 30 seconds, when a single fuel at different feed rates is being fed, to determine the maximum knock intensity feed signal for that fuel. Thus, a series of five knock intensity generations used to generate a maximum knock intensity fuel feed-rate setting can be completed in about 150 seconds. However, when a comparative octane number determination, involving a known fuel, an unknown fuel and a known fuel, as a series of runs, is being made, a relatively long signal measuring time is used, such as 1 minute, preferably after the knock intensity stabilizes. The stabilization time is about 3 minutes.

Such a comparative series of 3 new knock intensity signals comparing fuels can be completed in 12 minutes. To assure fair comparisons in a series, the engine operating time on each setting in the series should be the same. Preferably, each series of knock intensity generations is completed as quickly as possible to minimize the effect of engine drift on the comparison value of each generated knock intensity in the series.

Computers that would be operable in this invention are well-known. One such computer is Model PDP8E Digital Computer, sold by Digital Equipment Corp., Maynard, Massachusetts.

Octane numbers can be calculated from the knock intensity signals in various ways. It is preferred in this invention to calculate the unknown fuel octane number with calculating means adapted to solve the following equation:

$$ON = L + (H-L)(b-c/b-a)$$

where
$ON$ = octane number of the unknown fuel;
$H$ = octane number of the higher octane reference fuel;
$L$ = octane number of the lower octane reference fuel;
$c$ = knock intensity signal units from the unknown fuel;
$a$ = knock intensity signal units from the higher octane reference fuel;
$b$ = knock intensity signal units from the lower octane reference fuel.

FIG. 2 shows only one, 8, of a plurality of fuel reservoirs in communicating relation with fuel chamber bowl 41. Fuel container 57A inverted in container support 55 provides fuel 57 having a level 58. Container 57A (embodying reservoir 8) communicates with fuel feed chamber 41 (embodying chamber 9) by gravity feed through fuel line 59, tee 60, fuel-shut-off valve 39 and fuel line 42 having nozzle 42A. Line 42 is an embodiment of line 17 in FIG. 1. Chamber 41 communicates with fuel/air mixing venturi 26 through riser column 47, restricted orifice 49 and fuel line 50. The fuel feed-rate is variable (controlled by fuel-rate metering device 27) according to thread positioning by screw 52 of integral needle 48 in orifice 49. Screw 52 is responsive to geared-down stepping motor 51 at definite metering settings according to fuel metering rate control signals provided by control means 34 shown in FIG. 1.

Fuel feed-rate settings can be applied by means responsive to analog or, preferably, digital signals. True signal responses are easily attained in a screw-controlled needle valve by rotating the screw with a control motor having high torque. However, such guaranteed action can damage the setting reliability of a screw needle were it to jam the needle in the orifice. Thus, it is preferable to drive the screw by a relatively low torque and incorporate a measuring analog follower to signal that the actual feed setting is the setting directed by the control means. Thus, a stepping motor used to rotate a screw-controlled needle valve is easily checked by a potentiometer meshed to transmit a proportion of a constant applied voltage over the same range of screw turning, and the potentiometer voltage can be read in terms of the rate setting as checked.

In FIG. 2, valve 39 is responsive to a control signal which selects a particular feed for feeding into chamber 41. Chamber 41 has a low volume fuel holdup, say, about 0.04–0.5 cubic inches, and has overflow trough 44 surrounding it inside shell 43. Overflow lines 45 and 46 are in drain-off relation to trough 44. Nozzle 42A is disposed to direct a fuel into chamber 41 only when valve 39 is open and to drip into trough 44 should valve 39 leak when closed.

Line 59 is sufficiently large to purge bubbles present, and preferably is at least about 3/16 inch in inside diameter. Nozzle 42A of fuel line 42 is relatively small to insure that a fuel feed from it streams into chamber 41, e.g. up to about 0.035 inch inside diameter. Chamber 41 is able to carry an adequate fuel flow to the test engine without needing a large fuel container 57A to maintain a stable fuel head between level 58 and nozzle 42A.

Shut-off valve 39 is preferably oriented for fuel exit at its top side. It is preferably in heat exchange contact with cooling means 40, typically a tube of appropriate cross-section adapted to a flow of cooling liquid through it. Drain valve 61 allows the fuel to be quickly drained from reservoir 8, rinsed and replaced with a different fuel.

In the embodiment of FIG. 2 reservoir 57 provides gravity fuel flow through line 59, tee 60 up and out the top of solenoid-responsive valve 39, through line 42 and directly into chamber 41 when valve 39 is open. Fuel flow from nozzle 42A is made practically constant because variations of level 58 as a result of using fuel in container 57A are small (e.g. 1/8 inch) in comparison to the level difference (e.g. 3–6 inches) between level 58 and nozzle 42A. Lines 59 and 42, tee 60 and valve 39 are selected and arranged to have no zones where vapor can accumulate. Line 42 preferably extends a short distance vertically from the upper side of tee 60. Cooling means 40 helps to avoid vapor formation by avoiding fuel warm-up and to have no zones where liquid can accumulate during draining and rinsing through valve 61.

The fuel level maintained in chamber 41 has a constant head above the fuel exit at venturi 56. Chamber 41 is provided with a fuel flow from line 42, or any other like line from a reservoir not shown, adequate to keep fuel in chamber 41 overflowing. The low volume holdup of chamber 41 in combination with an overflow fuel feed to it enables the quick transition of engine operation from one fuel to another.

The automatic determination of the maximum knock intensity feed-rate of a fuel is exemplified in FIG. 4. A fuel is drawn into the engine through an orifice partly closed by a metering needle on the end of a micrometric computer-controlled screw, as shown in FIG. 2. The computer is programmed to set the screw at specified settings, to run the engine with the needle at each setting and to receive knock intensity signals representing engine operation on each setting, as for knock intensity points marked 1, 2, 3, 4 and 5.

The computer assumes a parabola with a vertical axis based on the highest signal and the signal on either side and calculates that a fuel feed setting at peak 1 would provide that knock intensity signal. The curve represents the parabola basis of peak 1. The approximate maximum knock intensity fuel feed setting so determined can be used in most cases as a basis for subsequent compared octane number determinations of most fuels. Its use results in acceptable octane numbers.

A refined maximum knock intensity feed-rate can be determined using peak No. 1 as a starting point. For this, the computer is programmed to adjust the needle to a narrower range of settings centered on the peak No. 1 setting and broad enough to span the region of greatest knock intensity signals, and to receive knock intensity signals representing engine operation on each setting. Such settings and their signals are marked 6, 7, 8 and 9.

If knock intensity at setting 7 is the highest measured, the knock intensities of setting 7 and adjacent settings 6 and 8 are used to develop a new parabola. If the knock intensity is highest at setting 8, as indicated by FIG. 4, the new parabola is developed from the knock intensities of setting 8 and adjacent settings 7 and 9.

From this new parabola, indicated by the dotted line, the computer determines that the fuel feed-rate setting at peak 2 would produce a refined maximum knock intensity signal. The refined maximum knock intensity fuel feed-rate setting so determined is used as a basis for subsequent compared octane number determinations. Its use results in very accurate octane numbers.

Described below is a typical process for determining octane numbers using the means combination of FIG. 1.

EXAMPLE

Reservoirs 1 and 8 are charged with reference fuels of known octane numbers and reservoirs 2 to 7 are charged with fuels of unknown octane numbers. The reference fuels are chosen so that their octane numbers encompass the anticipated octane number range of the unknown fuels. The levels of the reservoirs are above fuel entry points into chamber 9. The operational sequence, then, is as follows:

I. control means 34 opens valve 18 (reference fuel) and, in sequence, while it is open sends a series of, say five, different fuel feed-rate signals to rate metering means 27, each for a relatively short fixed time of about 20 to 40 preferably 30 seconds selected to encompass the maximum knock setting for any fuel, memory means 33 and calculating means 35 receive a knock intensity signal generated by engine operation on each feed-rate setting, calculating means 35 calculates the approximate fuel feed-rate setting at the point of maximum knock intensity from knock intensity signals and fuel feed-rate settings on a parabolic curve passing through the highest knock intensity signal received during the series, and calculating means 35 directs control means 34 to send to rate metering means 27 a series of fuel feed-rate settings above and below the approximate maximum knock intensity fuel feed-rate setting just calculated, each for a relatively short fixed time of about 20 to 40 seconds, preferably 30 seconds, and calculating means 35 calculates a refined maximum knock intensity fuel feed-rate setting from the parabolic curve passing through the refined highest knock intensity signal and adjacent lower knock intensity signals received during the series, then, calculating means 35 transfers the refined maximum knock intensity feed-rate setting to memory means 33 where it is correlated with the reservoir providing the fuel and stored, II. repeat the above, but each time with a different valve selected from valves 19 to 25, III. then valve 18 (reference fuel) is opened and while it is open the calculated maximum knock intensity feed-rate setting from means 33 is transmitted to means 27 for a time sufficient to result in a new knock intensity during a fixed time of about 1 minute after a knock stabilizing time of 3 minutes, and a new knock intensity signal is received in means 33 and 35 during the knock intensity measuring time, IV. repeat III with valve 19 open from reservoir 2 (a fuel of unknown octane number), and then with valve 25 open (the other reference fuel), V. repeat IV but interpose between the reference fuels, each of the remaining unknown fuels from reservoirs 3 to 7, transfer to means 35 the new knock intensity signals of each fuel from reservoirs 2 to 7 and its immediately preceding and succeeding reference fuel knock intensity signals according to III, IV and V, and calculate by means 35 the octane number of the unknown fuels according to their new knock intensity signals relative to the new knock intensity signals of the reference fuels measured immediately before and after each unknown fuel.

The test engine is set for proper operating conditions for the octane range chosen as will be appreciated by those skilled in the art employing such guides as, say, Test Method D-2699-Test for Knock Characteristics of Motor Fuels by the Research Method, D-2700-Test for Knock Characteristics of Motor and Aviation Type fuels by the Motor Method, as described in ASTM Manual for Rating Motor, Diesel and Aviation Fuels (1971).

The novel apparatus of this invention and the process taught herein for determining fuel octane numbers using fuel feed-rate settings which generate maximum knock intensities can operate on any number of fuel reservoirs to determine the octane numbers of the fuels contained therein. It has been found that the apparatus can automatically find 14 octane numbers within about 3½ hours.

The embodiments of the invention in which an exclusive property or privilege is claimed are defined as follows:

1. In a process for determining fuel octane numbers from knock intensity signals generated by a test engine by comparing knock intensities of fuels of unknown octane numbers against knock intensities of fuels of known octane numbers, the improvement comprising, in sequence, i. operating the test engine on each fuel at a series of feed-rate settings for a time sufficient to generate a knock intensity signal for each fuel at each of the feed-rate settings, said knock intensity signals bracketing the feed-rate setting which gives the maximum knock intensity for each fuel, ii. calculating the approximate setting for each fuel at which the maximum knock intensity signal is generated, iii. operating the engine on each fuel at a narrower series of feed-rate settings than employed in (i), such settings bracketing the approximate maximum knock intensity setting as determined in (ii), to produce a refined feed-rate setting at which the maximum knock intensity signal is generated for each fuel, iv. storing the refined feed-rate setting of maximum knock intensity, v. operating the test engine on each fuel at the stored refined feed-rate setting at which the maximum knock intensity is generated, for a time sufficient to generate a new knock intensity signal, the test engine being operated on the fuels of known and unknown octane numbers in alternating sequence, and vi. calculating the octane numbers of the fuels of unknown octane numbers by comparing the new knock intensity signals produced in (v).

* * * * *